United States Patent [19]
Stern

[11] Patent Number: 5,259,732
[45] Date of Patent: Nov. 9, 1993

[54] SYRINGE PUMP WITH SYRINGE BARREL POSITION DETECTOR

[75] Inventor: Carl M. Stern, Pennington, N.J.

[73] Assignee: Becton, Dickinson and Company, Franklin Lakes, N.J.

[21] Appl. No.: 875,920

[22] Filed: Apr. 29, 1992

[51] Int. Cl.⁵ ............................................. F04B 21/00
[52] U.S. Cl. ..................................... 417/63; 604/154; 128/DIG. 1
[58] Field of Search .................. 417/63; 604/151, 154; 128/DIG. 1

[56] References Cited

U.S. PATENT DOCUMENTS

| | | | |
|---|---|---|---|
| 4,424,720 | 1/1984 | Bucchianeri | 74/89.15 |
| 4,529,401 | 7/1985 | Leslie et al. | 604/131 |
| 4,544,369 | 10/1985 | Skakoon et al. | 604/155 |
| 4,560,979 | 12/1985 | Rosskopf | 604/154 |
| 4,624,658 | 11/1986 | Mardorf et al. | 604/154 |
| 4,627,835 | 12/1986 | Fenton, Jr. | 604/67 |
| 4,652,260 | 3/1987 | Fenton, Jr. et al. | 604/154 |
| 4,741,732 | 5/1988 | Crankshaw et al. | 604/50 |
| 4,767,406 | 8/1988 | Wadham et al. | 604/155 |
| 5,034,003 | 7/1991 | Denance | 604/155 |

FOREIGN PATENT DOCUMENTS

| | | |
|---|---|---|
| 0142736 | 5/1985 | European Pat. Off. . |
| 0354852 | 2/1990 | European Pat. Off. . |
| 0388102 | 9/1990 | European Pat. Off. . |
| 4-17863 | 1/1992 | Japan . |
| 8707843 | 12/1987 | PCT Int'l Appl. . |
| 2109242 | 6/1983 | United Kingdom . |
| 1465797 | 3/1987 | United Kingdom . |

Primary Examiner—Richard A. Bertsch
Assistant Examiner—Charles C. Freay
Attorney, Agent, or Firm—Michael G. Schwarz

[57] ABSTRACT

A belt driven infusion pump for emptying the contents of a syringe is disclosed. The pump includes a syringe pusher including an anti-siphon catch and a pressure detector which is used for detecting occlusions or the end of infusion. A syringe clamp for locking a syringe in place is also provided. The syringe clamp is spring-loaded and lockable. A syringe position detector is provided to ensure the proper placement of the syringe prior to and during pumping. A control knob is provided on the face of the pump for controlling both the locking of the syringe barrel clamp and the coupling of the drive belt with a d.c. motor. The pump includes a housing having an elongated slot through which the syringe pusher is connected to the drive belt. A sealing band is connected to the syringe pusher and is moveable with the syringe pusher for sealing the slot against moisture or other contaminants. A pole clamp assembly is incorporated within the pump housing and includes a clamping arm for securing the pole between the clamping arm and the housing. The clamping arm is movable to a storage position where it is substantially flush with the outer surface of the pump housing.

9 Claims, 16 Drawing Sheets

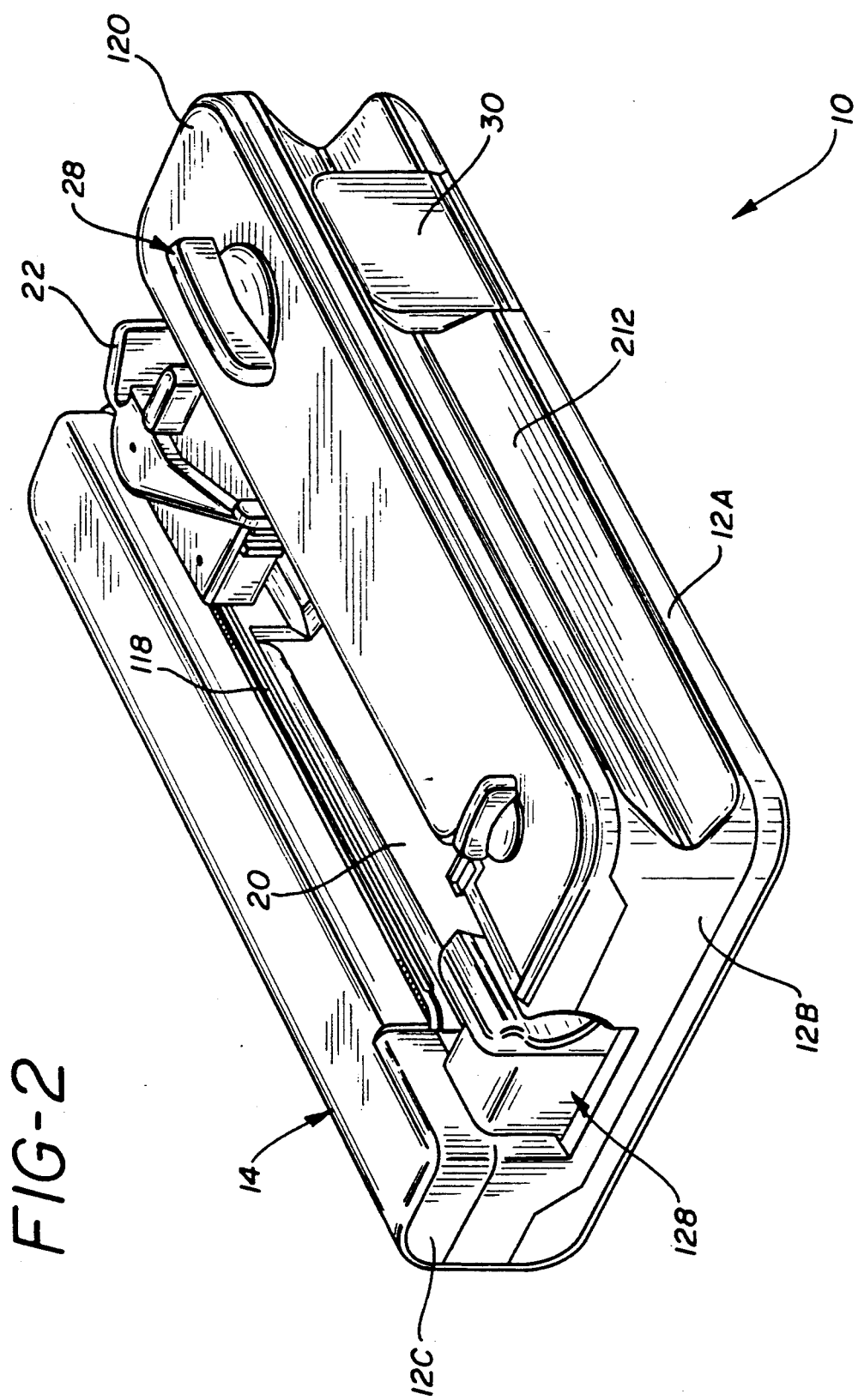

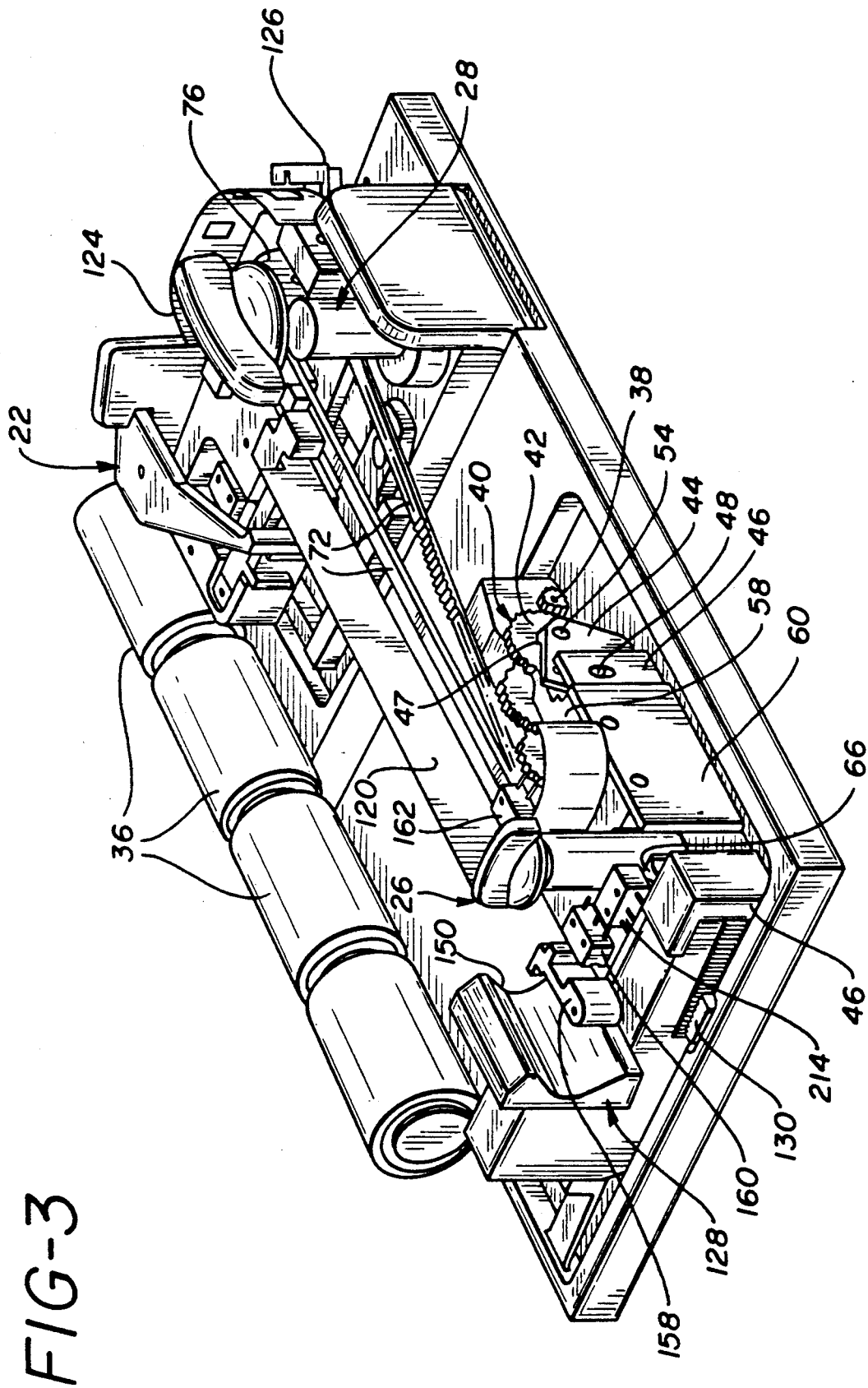

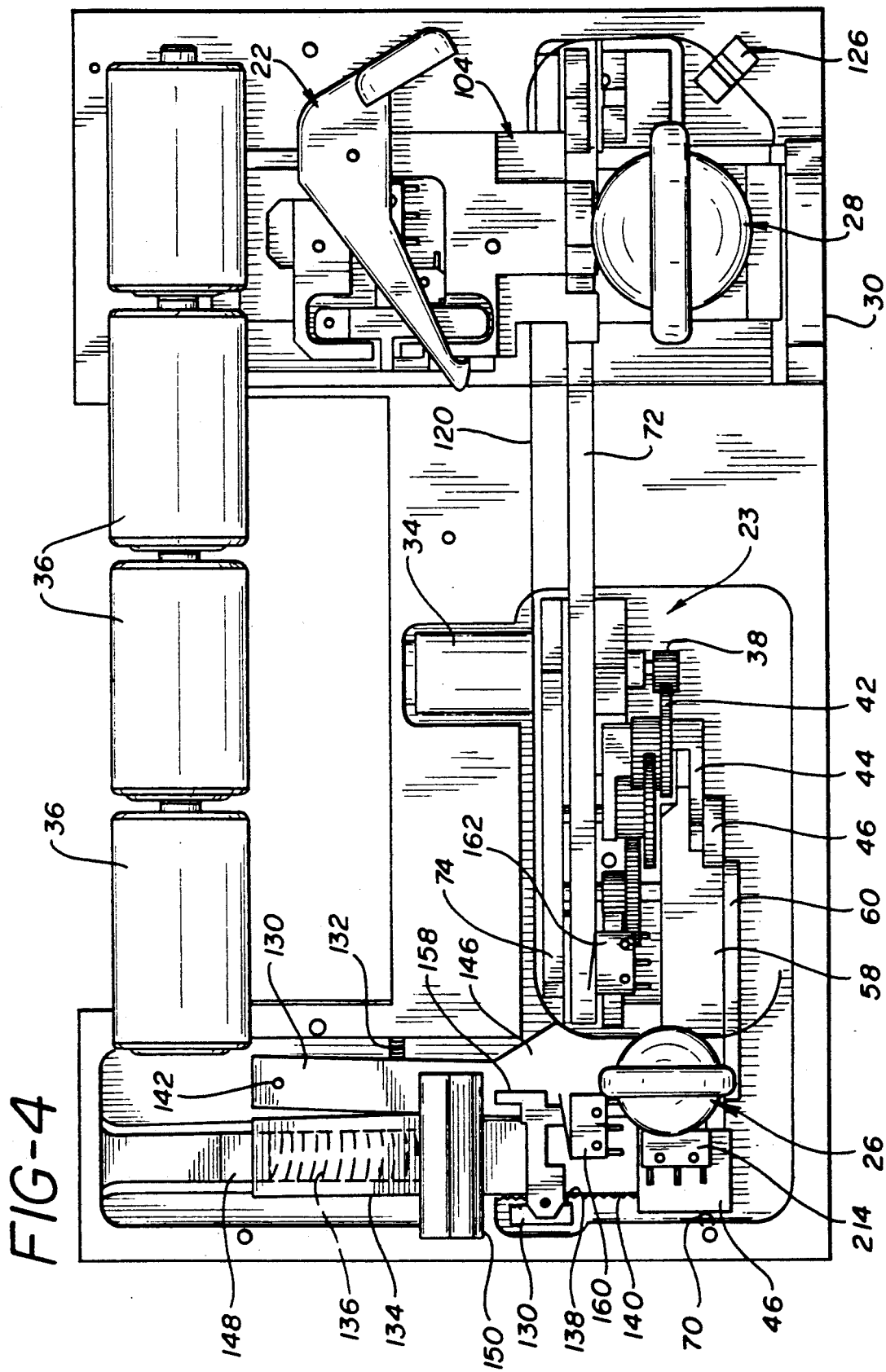

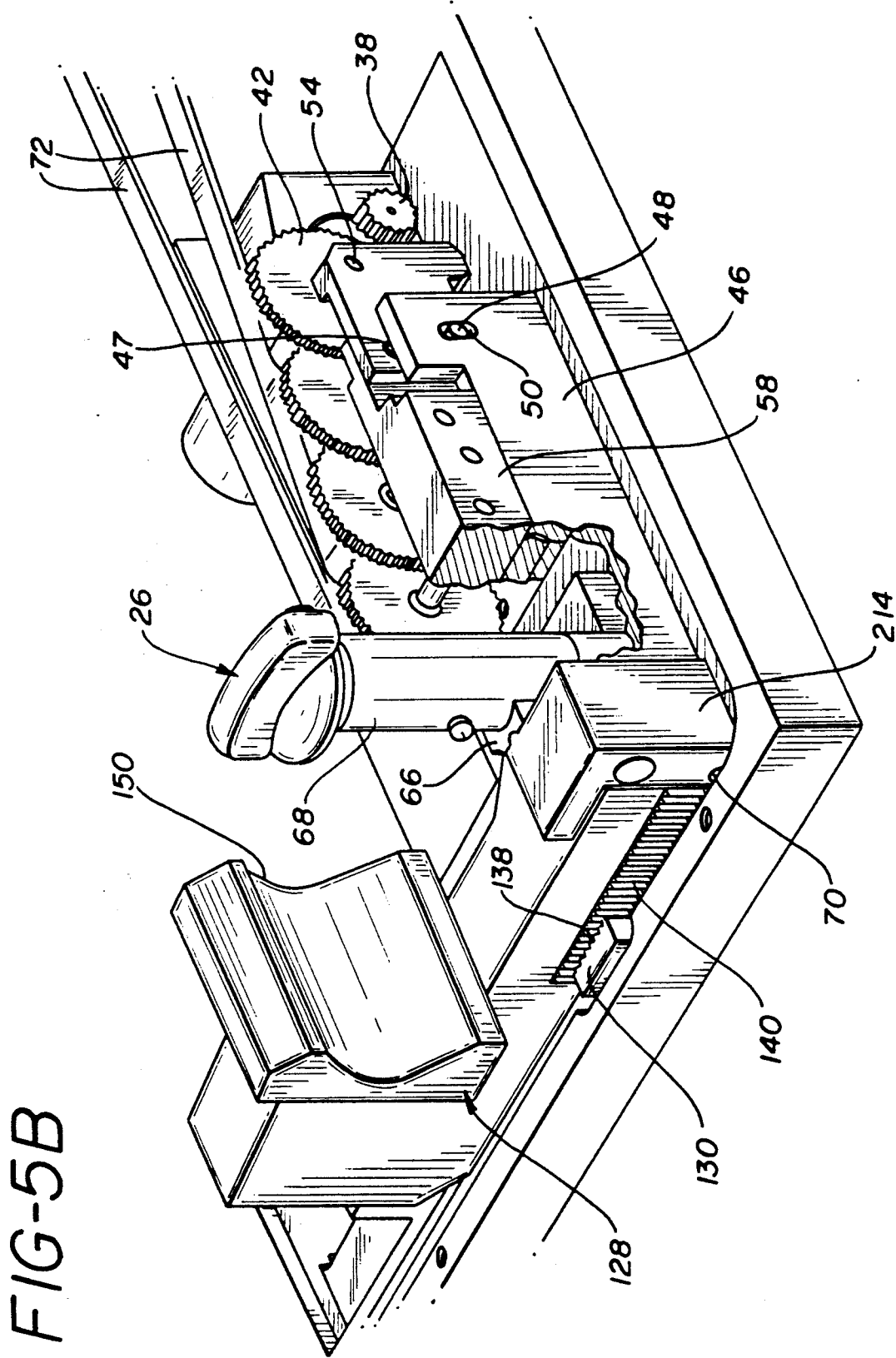

FIG-13
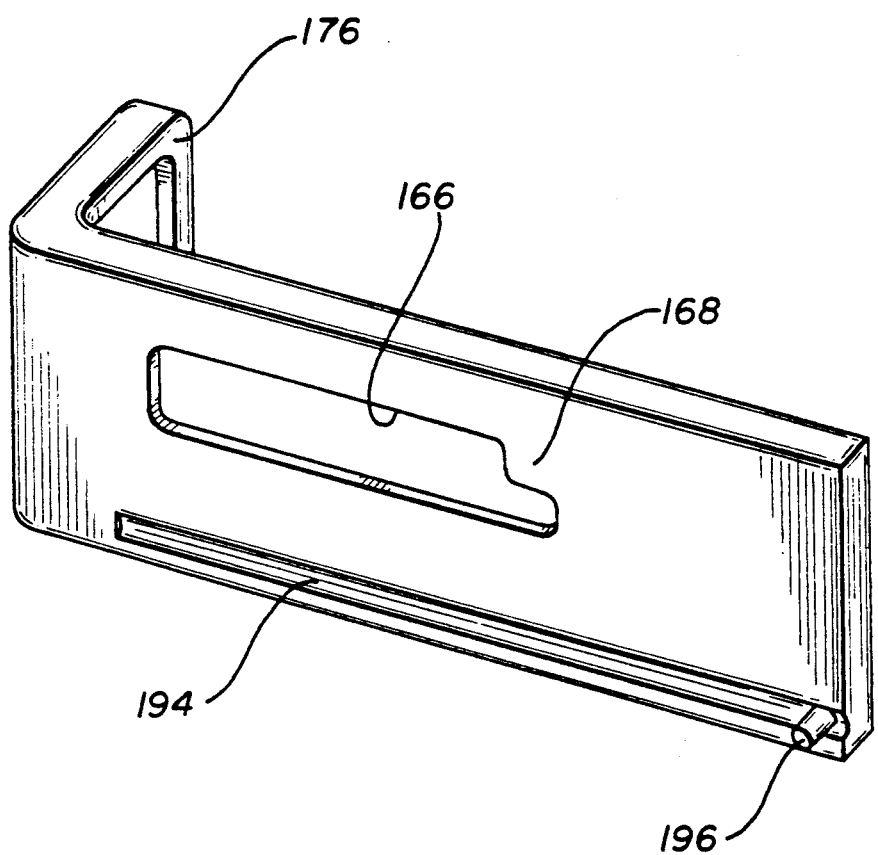
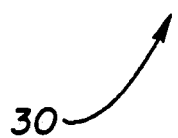

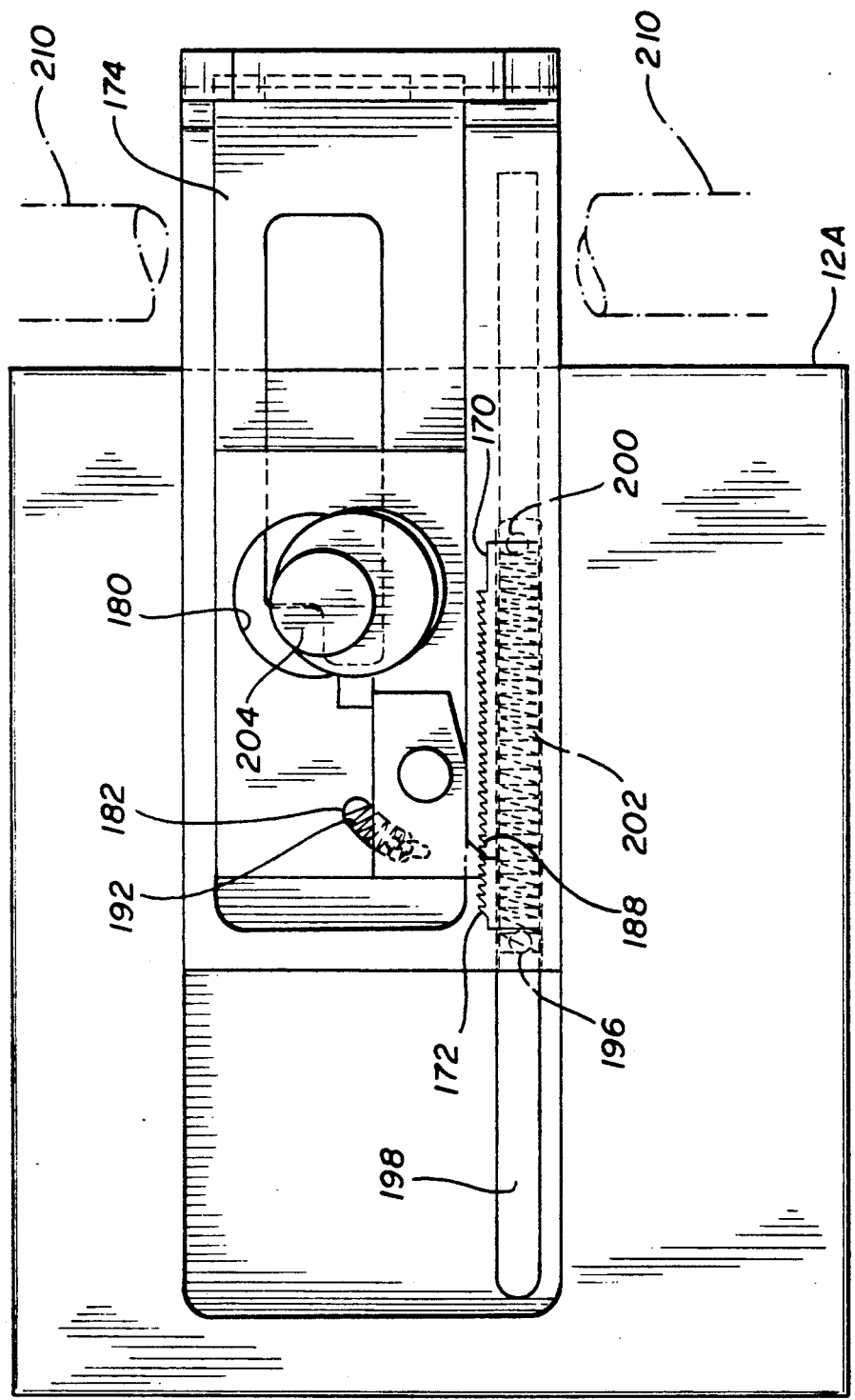

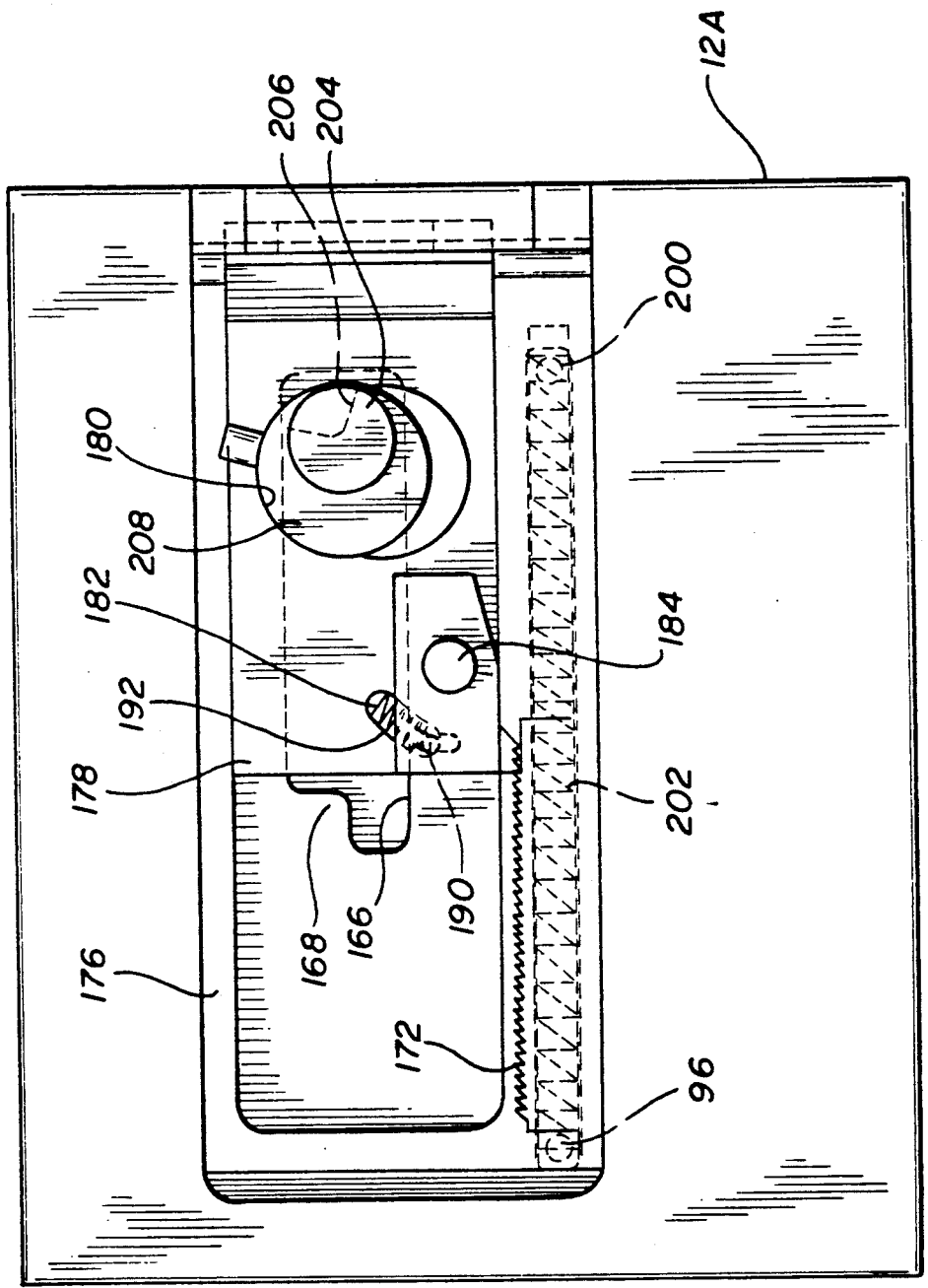

SYRINGE PUMP WITH SYRINGE BARREL POSITION DETECTOR

BACKGROUND OF THE INVENTION

This invention relates to syringe pumps. A syringe pump is a device used in the medical field for pumping liquid such as medication from a syringe into a patient. A syringe pump typically includes a housing, a mechanism for holding a syringe in place and a mechanism for pushing the plunger of the syringe so that the liquid is infused into the patient.

In order for a syringe pump to function correctly, the syringe must be properly placed in the pump. An improperly placed syringe may result in an error in the infusion of the liquid. It is therefore an object of this invention to provide a syringe pump equipped with a device for detecting a syringe so that if the syringe is improperly placed an alarm is generated or the syringe pump will not function.

SUMMARY

The invention is a syringe pump equipped with a device for detecting a syringe and for insuring that the syringe is correctly placed in the syringe pump. The device is typically integral with the syringe pump housing. It is typically part of a wall of the syringe pump housing against which the syringe can be placed. The wall is provided with a projection which projects outward from the wall. The projection projects a distance which is approximately equal to the thickness of the cylindrical wall forming the barrel of the syringe. If the syringe is improperly placed, the projection will abut against the syringe barrel. If a syringe is placed against the wall in the correct position for infusion, the projection will not abut the barrel of the syringe. Rather, the syringe will be oriented such that the projection projects towards the syringe plunger, perpendicular to the wall. Since the projection projects a distance approximately equal to the thickness of the cylindrical wall, the projection will almost reach the plunger but will not obstruct the plunger.

A detector is provided for detecting the syringe barrel. If the syringe is properly placed, the barrel will abut the detector. If the syringe is improperly placed, the barrel will not be able to touch the detector because of the presence of the projection. The detector is mounted adjacent the projection in order to prevent the barrel from touching the detector unless the syringe is properly placed. The wall of the syringe pump is preferably provided with a recess into which the syringe flange fits when the syringe is properly placed.

BRIEF DESCRIPTION OF THE DRAWINGS

FIG. 2 is a top perspective view of the infusion pump as viewed from the right hand side of the pump of FIG. 1;

FIG. 3 is a top perspective view of the infusion pump viewed from the same point as in FIG. 2 but with the upper housing elements removed;

FIG. 4 is a top plan view of the infusion pump with the upper housing elements removed;

FIG. 5B is a close-up perspective view of the syringe holder and drive assembly engagement mechanism in an engaged state with part of the mechanism cut away for clarity;

FIG. 13 is a rear perspective view of the clamp part of the pole clamp assembly;

FIG. 14A is a top plan view of the pole clamp assembly in the open position;

FIG. 14B is a top plan view of the pole clamp in the closed position;

DETAILED DESCRIPTION

Figure 1:
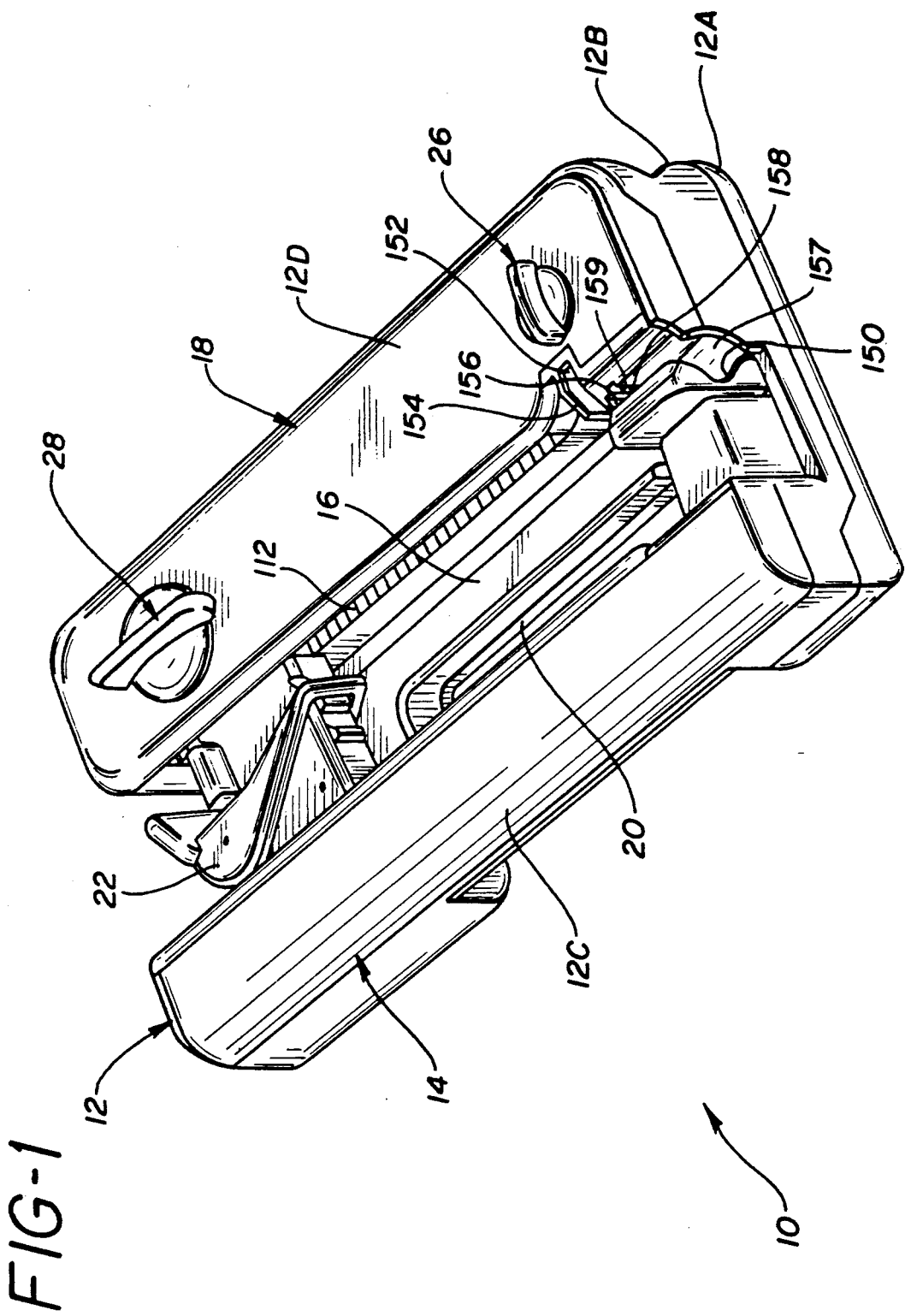
FIG. 1 is a top perspective view of the preferred embodiment of an infusion pump according to the invention.
Figure 5A:
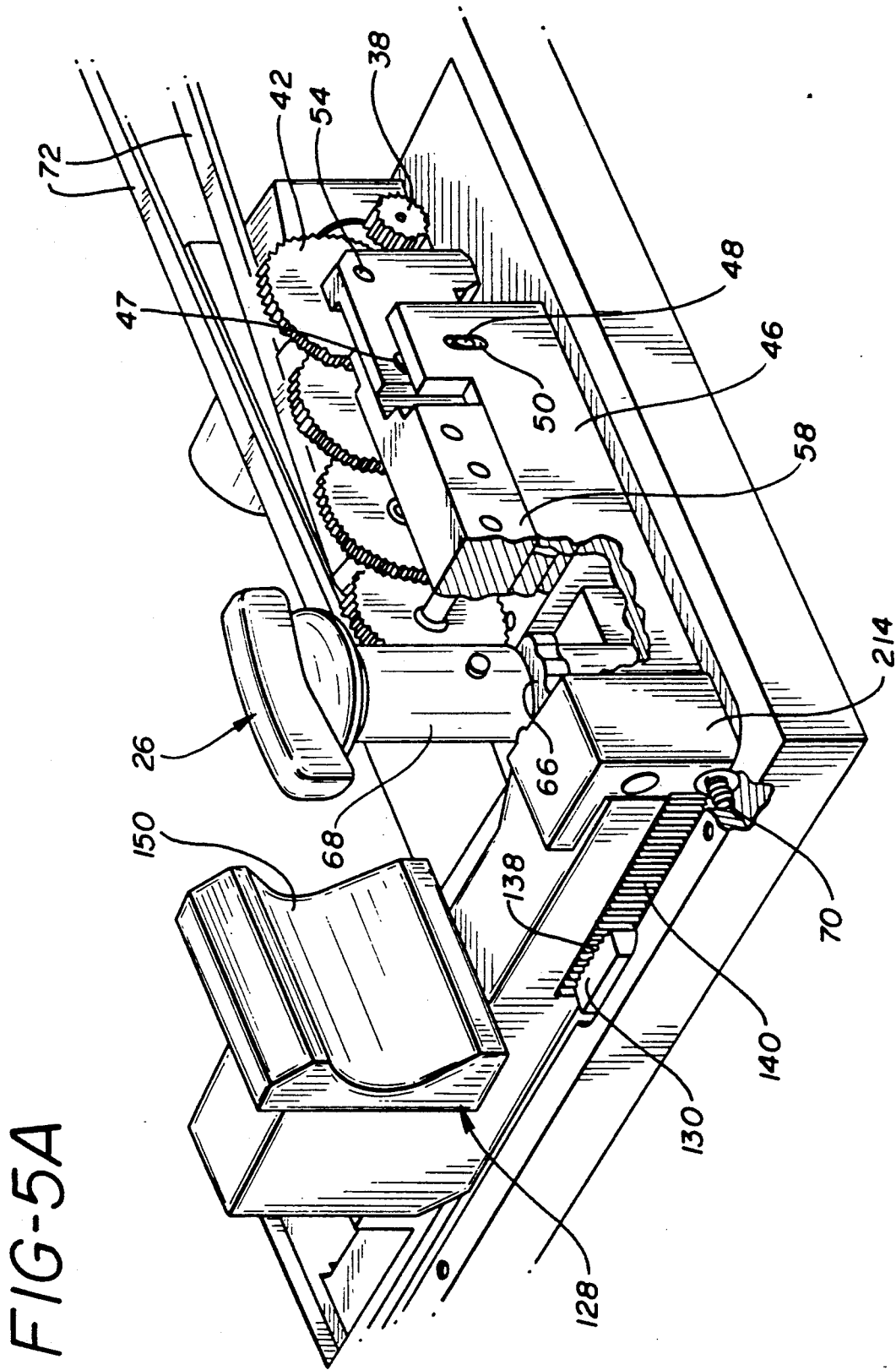
FIG. 5A is a close up perspective view of the syringe holder and drive assembly engagement mechanism in a disengaged state with part of the mechanism cut away for clarity.
Figure 6:
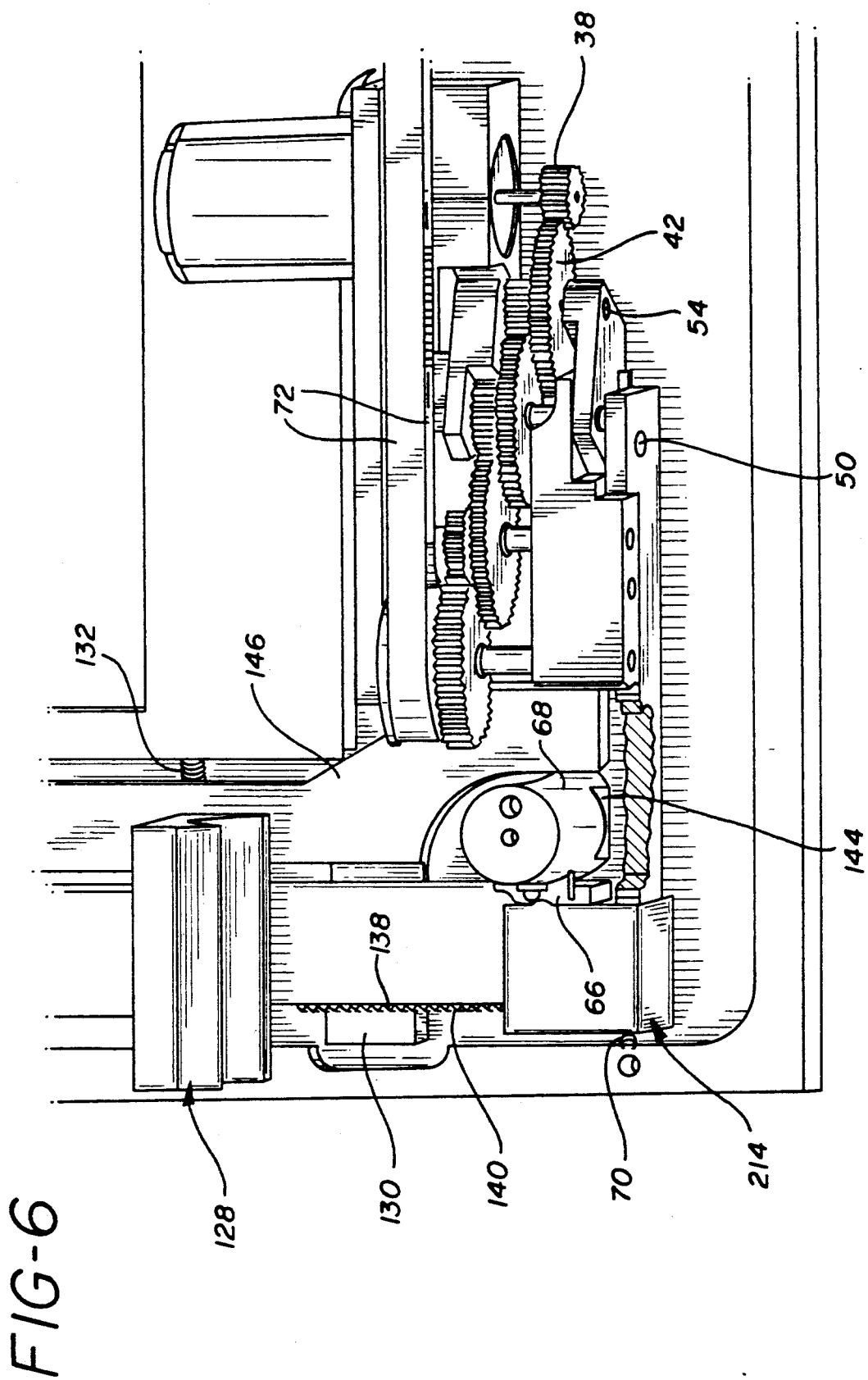
FIG. 6 is a top perspective view of the syringe holder and drive assembly engagement mechanism with part of the mechanism cut away for clarity.

A preferred embodiment of the invention is shown in the drawings and will herein be described in detail. Referring to FIGS. 1 and 2, an infusion pump 10 is provided for causing fluid to be pumped from a syringe. A pump of this general type is disclosed in U.S. Pat. No. 4,838,857, which is incorporated by reference herein. Such pumps are frequently employed for administering drugs such as antibiotics over a time. They are preferably capable of accepting several sizes of syringes.

Pump 10 includes a housing 12 which is made from a durable, light-weight material. Housing 12 comprises a base 12A, a mid-housing 12B, a battery compartment cover 12C and a drive mechanism compartment cover 12D. An integral handle 14, which may also function as a battery compartment, is defined by one portion of the housing. A recess 16 is defined by handle 14, drive mechanism compartment 18, and a portion of base 12A. Recess 16 includes an elongate opening 20 which facilitates use of handle 14. A syringe pusher 22 is also positioned within recess 16. Syringe pusher 22 is adapted for engaging the flanged end of a syringe plunger and moving the plunger within the barrel of a syringe. The operation of the pusher is described in greater detail below. The recess has an elongated configuration of suitable length and width for accommodating a variety of syringe sizes.

A pair of control knobs is provided on the front face of the housing. A first knob 26 is used for controlling the pump driving mechanism and a syringe clamp to hold the syringe in place during pumping, both of which are discussed below. A second knob 28 is used to lock and unlock a pole clamp 30, as shown in FIG. 2. Pole clamp 30 is used for securing the pump to an I.V. pole or a rail (not shown).

Referring to FIGS. 3 and 4, a belt/pulley drive mechanism 23 is employed for driving syringe pusher 22. The drive mechanism 23 includes gear assembly 40 and a d.c. motor 34 including an integral reduction assembly. While a stepper motor could alternatively be employed, a d.c. motor is preferred as it requires less power and is controllable in a less expensive and complex manner than a stepper motor. Motor 34 is powered by an appropriate power source such as the four batteries 36 shown in FIGS. 3 and 4. The motor may have an integral reduction gear assembly which drives pinion 38. The output shaft of the motor includes pinion 38 which is engageable with a gear reduction assembly 40 which provides a substantial overall gear reduction. A reduction on the order of about 15,000:1 is provided by the combined operations of the integral reduction assembly of motor 34 and gear reduction assembly 40.

Figure 8:
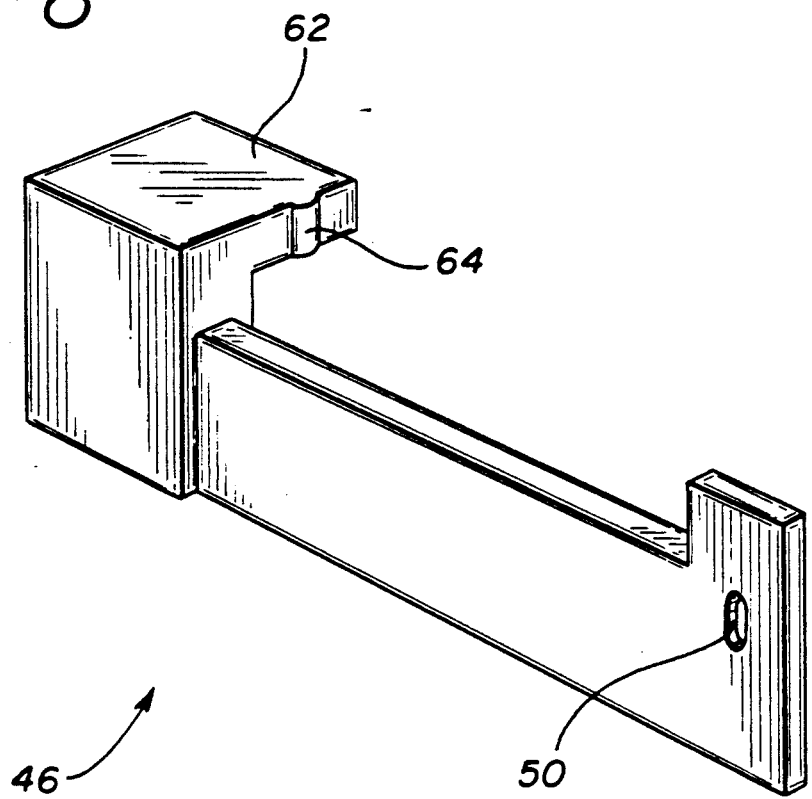
FIG. 8 is a top perspective view of the disengage link of the preferred embodiment.
Figure 9A:
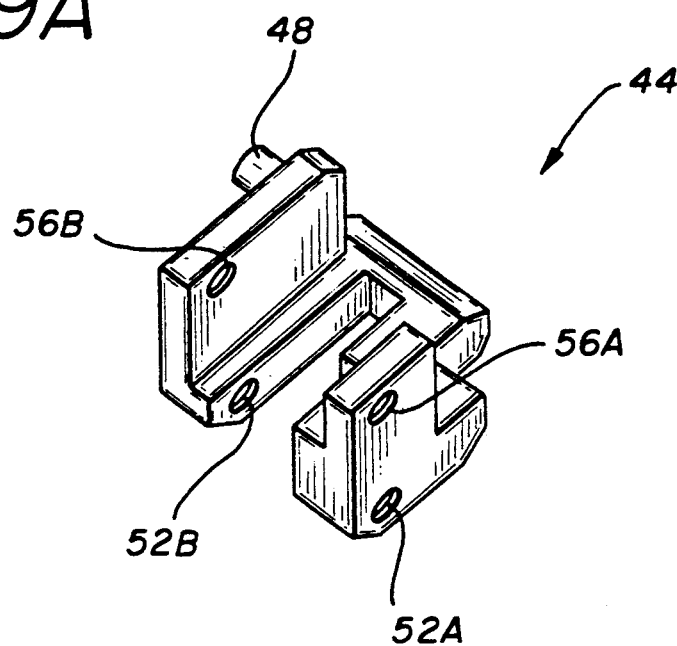
FIG. 9A is a perspective view of the cradle used in the drive assembly engagement mechanism of the preferred embodiment.
Figure 9B:
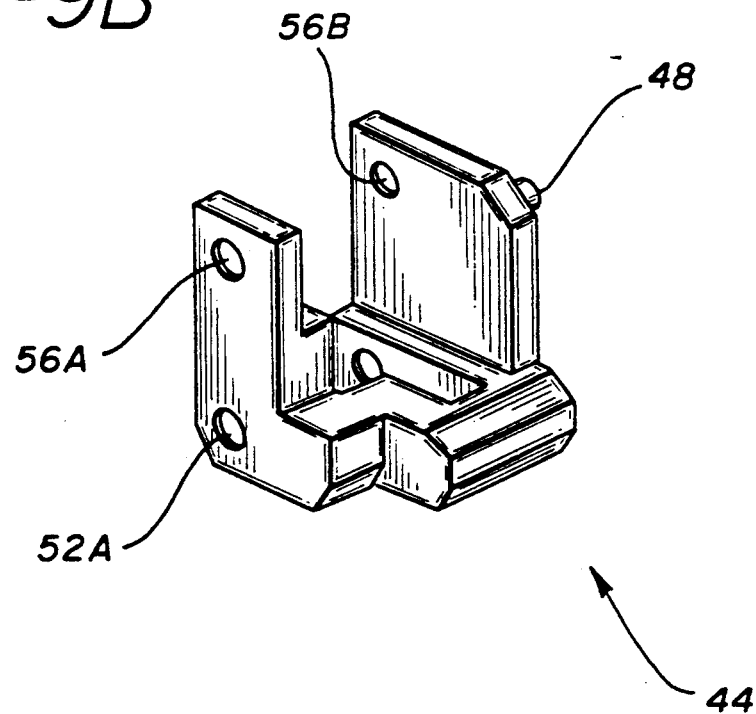
FIG. 9B is a top perspective view of the cradle taken from a different angle.

Gear 42 nearest to pinion 38 is mounted to a cradle 44, as shown in FIGS. 5A, 5B, 6, 9A and 9B. Cradle 44 is pivotably secured to a disengage link 46, which is shown in detail in FIG. 8. A peg 48 extending from cradle 44 is positioned within a slotted opening 50 within disengage link 46. A first set of opposing openings 52A, 52B within cradle 44 receives shaft 54 about which gear 42 rotates. A second set of openings 56A, 56B allows cradle 44 to be pivotably secured by pin 47 to a projection 58 extending from base 12A. Longitudinal movement of disengage link 46 accordingly causes cradle 44 to pivot about an axis extending through pin 47. Cradle 44 and disengage link 46 and their associated shafts, pins, springs and accessories are collectively referred to as "engagement means."

Disengage link 46 is positioned between projection 58 and a wall 60 which extends from base 12A. The end of disengage link 46 opposite from slotted opening 50 includes a laterally extending wall 62 having a rounded projection 64 extending from an edge portion thereof (See FIG. 6 which shows wall 60 and part of disengage link 46 cut away for clarity). Camming projection 64 is engageable with either of two notches formed in a wall 66 extending radially from shaft 68 of the control knob 26, depending upon the rotational position of control knob 26.

As shown in FIG. 4, disengage link 46 is urged in the direction of pinion 38 by a coil spring 70. When projection 64 is not positioned within one of the notches of wall 66, cradle 44 is in a generally upright position and gear 42 is disengaged from pinion 38. (See FIG. 5A which shows wall 60 removed and part of disengage link 46 cut away for clarity). Rotation of control knob 26 to a position where projection 64 moves into the notches of wall 66 causes the movement of disengage link 46 away from pinion 38. Cradle 44 accordingly rotates about pin 47, causing gear 42 to engage pinion 38. (See FIG. 5B which shows wall 60 removed and part of disengage link 46 cut away for clarity). A person of ordinary skill in the art will recognize that the means for engaging the motor and drive mechanism may be implemented in several equivalent ways, including by a clutch mechanism.

The drive mechanism for the pump includes an endless belt 72 which is supported by a drive pulley 74 and an idler pulley 76. Both pulleys are supported by the walls of base 12A. Drive pulley 74 is engaged with gear reduction assembly 40 and driven thereby. Syringe pusher 22 is secured to belt 72. As discussed above, first knob 26 controls the engagement and disengagement of pinion 38 and gear 42. When engaged, syringe pusher 22 can only be moved upon rotation of pinion 38. Neither syringe pusher 22 nor belt 72 can be moved manually at this time. When disengaged, syringe pusher 22 can be moved manually to a selected position as gear reduction assembly 40 provides little frictional resistance to rotation of belt 72. This allows pusher 22 to be moved within recess 20 with little resistance. A syringe can thus be easily positioned within recess 16 without obstruction.

Referring again to FIGS. 3 and 4, a clamp assembly 128 for clamping a syringe barrel is shown. In the prior art, such assemblies have generally included heavy springs to maintain a syringe in place. Because the user must open the clamp assembly to insert or remove a syringe, the force exerted by the spring must be limited to permit ease of use. Lower spring forces do not, however, provide effective holding capability. An alternative syringe clamp of the prior art includes a clamp operated by a screw. Such a device is cumbersome and it takes a long time to open and close such a clamp. Existing assemblies accordingly involve compromises due to these contradictory objectives.

The clamp assembly 128 in accordance with the invention provides both security and ease of use without compromising either feature. It includes a locking mechanism comprising a toothed member 130 which is pivotably secured to base 12A, a spring 132 for resiliently urging toothed member 130 about an axis of rotation, a clamping slide 134 for engaging a syringe barrel, and a spring 136 for resiliently urging the slide in a selected direction.

Toothed member 130 preferably includes a toothed surface 138, as best shown in FIG. 4. This surface is located in opposing relation to a toothed surface 140 of clamping slide 134. Toothed member 130 is pivotable about a pin 142 such that the toothed surface of toothed member 130 is movable into and out of engagement with the toothed surface of the slide. Spring 132 urges the toothed member out of engagement with clamping slide 134.

Figure 7:
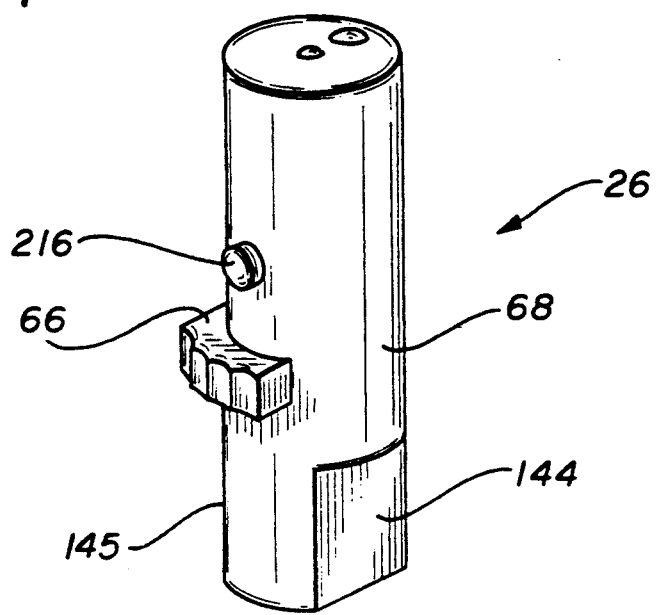
FIG. 7 is a top perspective view of the control knob shaft of the preferred embodiment.

Referring to FIG. 7, shaft 68 of control knob 26 includes a flat longitudinal surface 144 at the bottom thereof, the remainder of shaft 68 being a substantially cylindrical camming surface 145. Toothed member 130 includes an arm 146 which adjoins the bottom portion of shaft 68. The rotational position of flat surface 144 determines whether arm 146 engages the flat or cylindrical surface of shaft 68. If flat surface 144 is moved into opposing relation with arm 146, spring 132 causes toothed member 130 to move out of engagement with slide 134. Rotation of shaft 68 causes the cylindrical surface to engage arm 146, thereby rotating toothed member 130 about pin 142 and into engagement with slide 134.

Slide 134 houses spring 136 which causes it to move into engagement with a syringe barrel. Spring 136 extends between a projection 148 extending from base 12A and an inner wall of slide 134. Slide 134 includes a face portion 150 having an arcuate surface for accommodating a syringe barrel. Face portion 150 extends vertically with respect to base 12A and is positioned within recess 16.

While a linear slide 134 is disclosed, a person of ordinary skill in the art would be able to implement this aspect of the invention in several equivalent ways, for example by substituting a rotatable clamping member for slide 134.

The orientation of wall 66, flat portion 144 and camming surface 145 of shaft 68 determine the order of the engagement of gear 42 with pinion 38 and toothed member 130 with toothed surface 140. Wall 66, flat portion 144 and camming surface 145 can be oriented such that (1) gear 42 and pinion 38 mesh simultaneously with each other when flat portion 144 causes toothed member 130 to engage with toothed surface 140; (2) gear 42 and pinion 38 mesh only once toothed member 130 and toothed surface 140 engage or (3) gear 42 and pinion 38 mesh before toothed member 130 and toothed surface 140 engage. Wall 66, flat portion 144 and camming surface 145 can also be oriented so that gear 42 and pinion 38 can be engaged and disengaged while toothed member 130 and toothed surface 140 remain engaged. The preferred embodiment option (1) is described herein with the understanding that a person of ordinary skill in the art would easily be able to modify the device to accomplish options (2) and (3).

The same result could also be achieved by a person or ordinary skill in the art by substituting an equivalent electrical or electromagnetic system for the mechanical system disclosed herein to engage and disengage the drive mechanism and to lock and unlock slide 134.

Before or after securing the pump 10 to the pole control knob 26 is turned to a "release" position if not already in such a position. A filled syringe is positioned in recess 16 of the pump housing such that the flange of the syringe barrel extends within slot 152. Syringe pusher 22 is then manually engaged and moved into position against the flanged end of the syringe plunger. The flange of the syringe plunger is clamped between lip 82 of the swing arm 80 and one of the projections 94, 96 extending from bottom wall 98 of the pusher housing.

When in the "release" position, notched wall 66 extending from shaft 68 of control knob 26 exerts no pressure upon the disengage link 46. Coil spring 70 accordingly positions disengage link 46 such that cradle 44 is substantially upright and gear 42 of gear reduction assembly 40 is disengaged from pinion 38 extending from d.c. motor 34. In addition, toothed member 130 rides upon flat surface 144 of the shaft of control knob 26, allowing spring 132 to maintain toothed member 130 out of engagement with slide 134 of syringe clamp assembly 128. The on-off switch for the motor is, of course, in the "off" mode at this time due to the position of motor on/off switch 214 with respect to a switch actuating peg 216 which extends radially from the shaft of control knob 26. On-off switch 214 is shown as actuated by control knob 26, but can of course be actuated by a separate control.

Two additional settings are provided in accordance with the preferred embodiment of the invention, "motor off" and "motor run". When control knob 26 is turned from "release" to "motor off", the curved portion of the bottom of shaft 68 engages toothed member 130, thereby urging it into engagement with slide 134 of syringe clamp assembly 128. Radially extending wall 66 of shaft 68 simultaneously engages laterally extending wall 62 of disengage link 46, urging disengage link 46 away from gear assembly 40. These two actions cause syringe clamp assembly 128 to be locked in position and gear reduction assembly 40 to engage pinion 38 via gear 42 mounted to the cradle 44. Control knob 26 is maintained in the "motor off" position as one of the two notches within wall 66 receives rounded projection 64 of disengage link 46.

Control knob 26 may be turned to a second detent (run) position wherein rounded projection 64 moves within the second notch of wall 66 extending radially from control knob shaft 68. The positions of disengage link 46 and toothed member 130 are the same whether control knob 26 is in the "motor off" or "motor run" position. When moved to the "run" position, however, peg 216 extending from the shaft 68 of control knob 26 engages motor on/off switch 214, thereby causing motor 34 to operate.

It is important to insure that a syringe is properly positioned prior to operating the pump. Both the plunger flange and the syringe barrel flange must be properly engaged to insure proper positioning. The system for detecting whether the plunger flange is properly engaged is described below with respect to syringe pusher 22. Means are also provided for insuring that the syringe barrel flange is properly positioned before the motor 34 is allowed to operate.

Figure 10A:
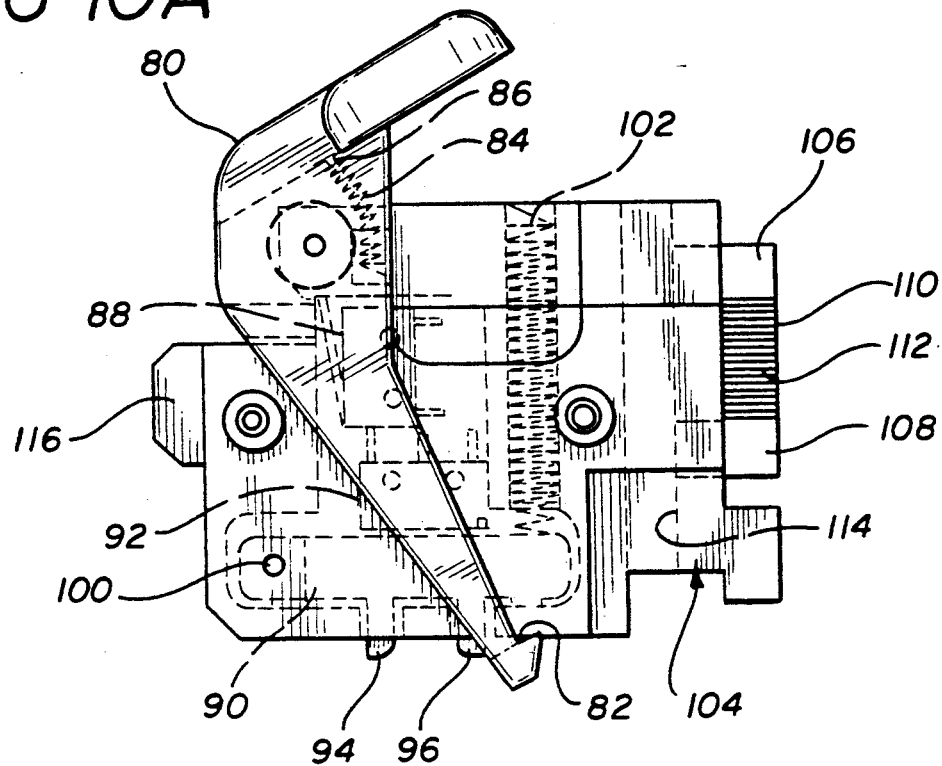
FIG. 10A is a top plan view of the syringe pusher.
Figure 10B:
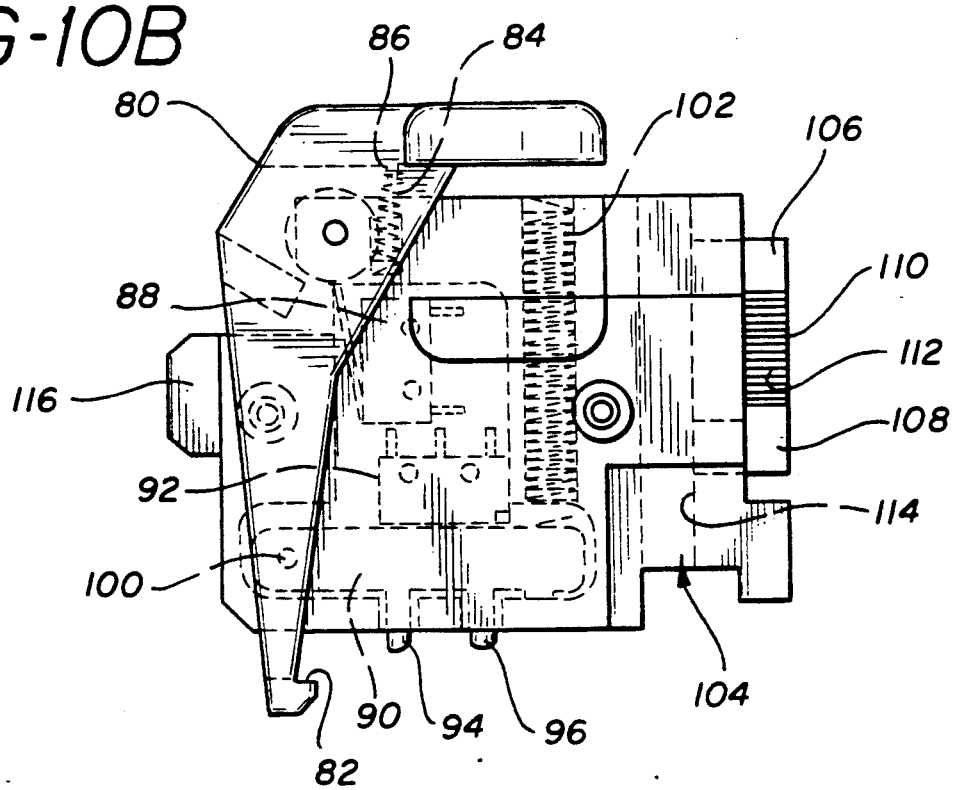
FIG. 10B is a top plan view of the syringe pusher showing the pusher swing arm in a different position from that shown in FIG. 10A.
Figure 11:
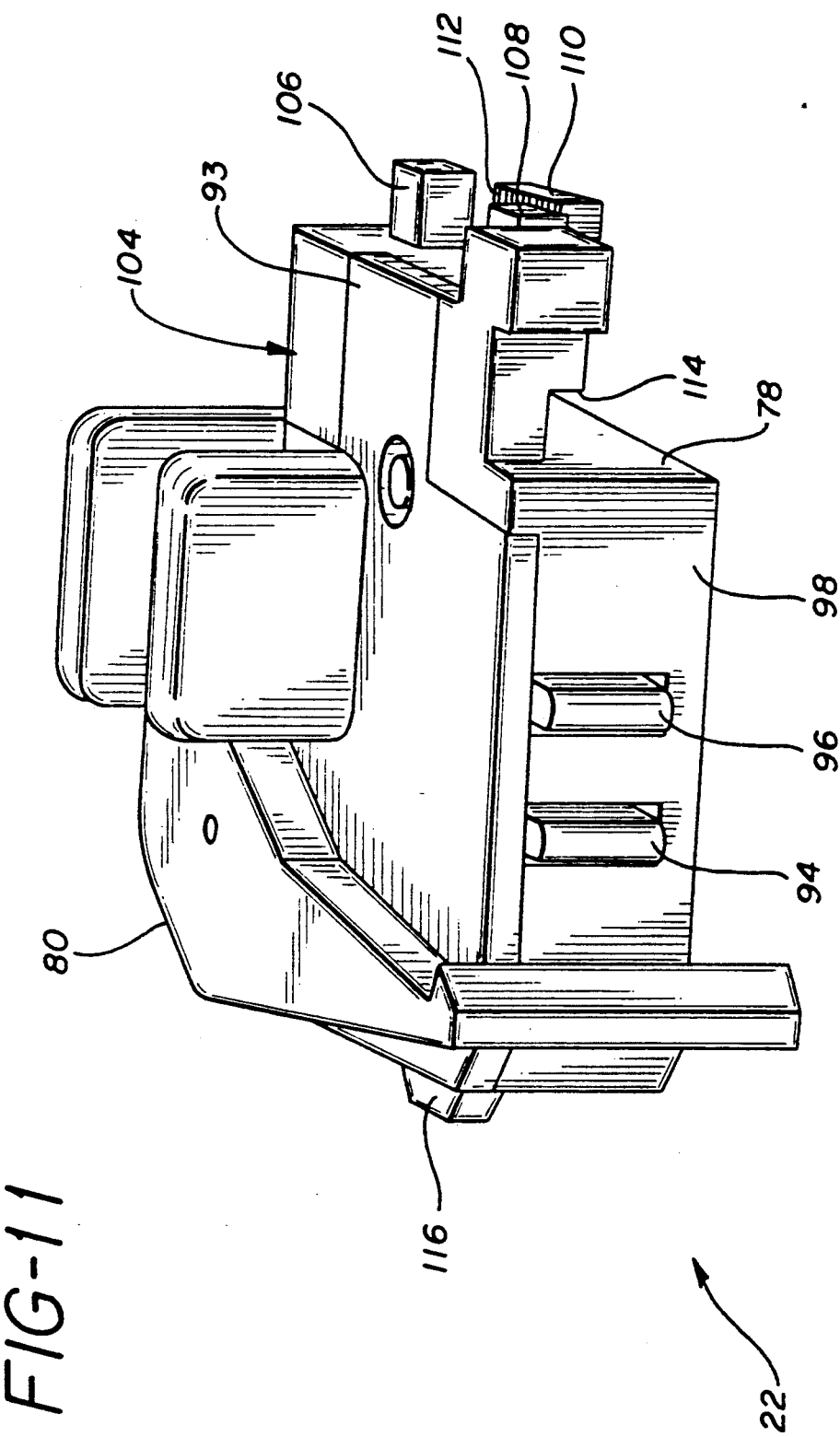
FIG. 11 is a bottom perspective view the syringe pusher.
Figure 12:
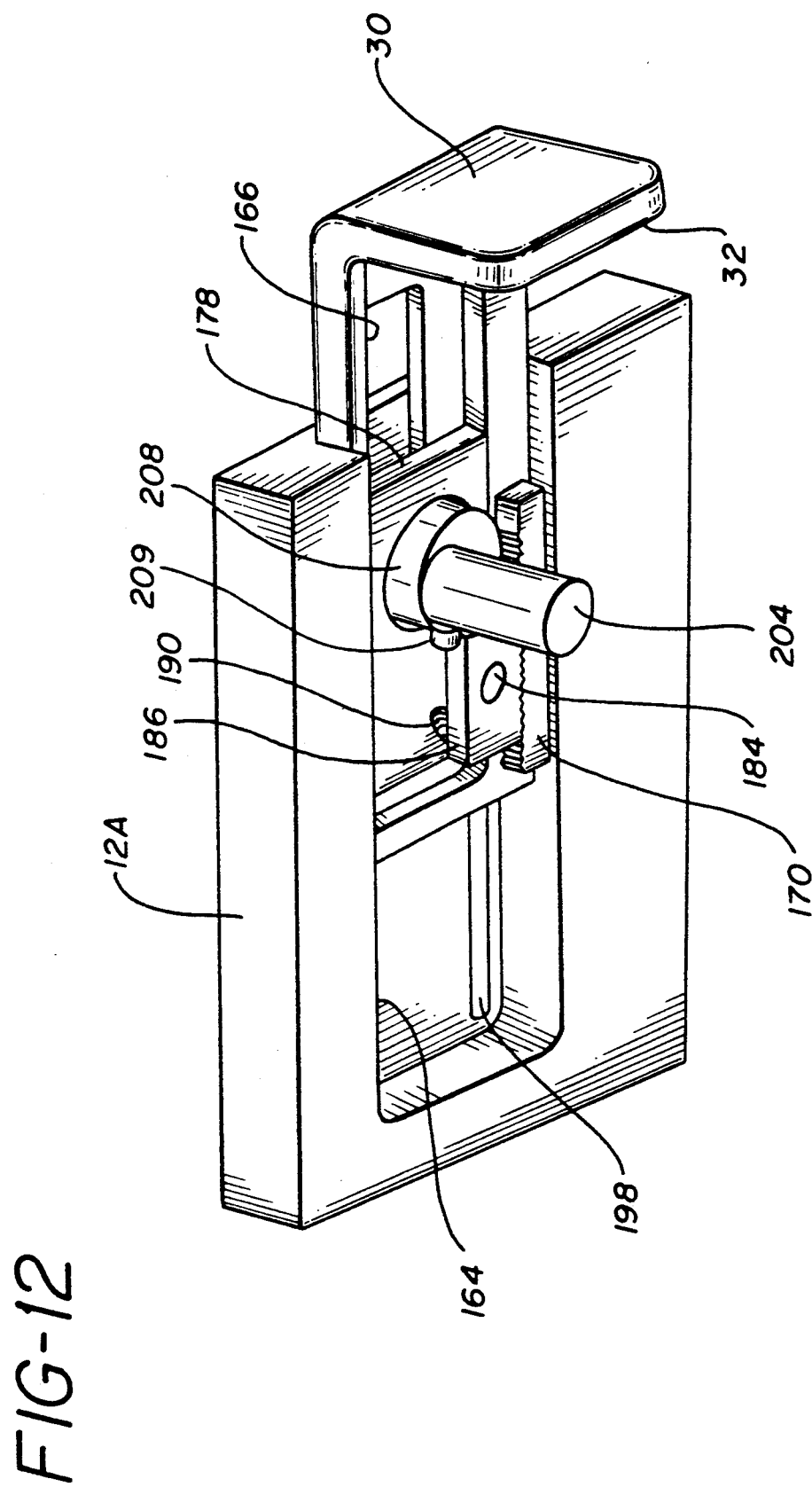
FIG. 12 is a top perspective view of the pole clamp assembly.

Syringe pusher 22 is shown in greatest detail in FIGS. 10A, 10B and 11. FIG. 10B shows pusher 22 as positioned when engaging the flanged end of a syringe plunger while FIG. 10A shows it in the fully closed position where no plunger would be engaged.

Syringe pusher 22 includes a housing 78 to which a swing arm 80 is pivotably mounted. Swing arm 80 includes a lip 82 suitable for engaging the flange of a syringe plunger. A spring 84 is secured to a peg 86 extending from the opposite end of swing arm 80, and urges it towards the position shown in FIG. 10A. A first switch 88 is mounted to housing 78 for detecting the position of swing arm 80. Different signals are accordingly provided depending upon whether arm 80 is in the position shown in FIG. 10A or FIG. 10B. The presence or absence of a syringe may accordingly be detected. In addition, the user will be alerted as to whether the syringe plunger flange is properly engaged. The latter feature is important in that swing arm 80 provides anti-siphon protection. In other words, the syringe plunger cannot be moved on its own while clamped to syringe pusher 22 and while motor pinion 38 is engaged as described above.

A lever 90 is also pivotably mounted to syringe pusher housing 78. Lever 90 is positioned adjacent to a second switch 92 which provides a signal when an occlusion is detected or when the syringe plunger has reached the end of the bottom of the syringe barrel. A cover 93 is secured to housing 78 for protecting lever 90 and switches 88, 92.

A pair of projections 94, 96 is secured to lever 90 and extends through a pair of openings in bottom wall 98 of housing 78. First projection 94 is longer than second projection 96 and is positioned closer to pivot 100 about which lever 90 rotates. A spring 102 resiliently urges lever 90 towards bottom wall 98 of housing 78. It will be appreciated that a greater force is required to move lever 90 when first projection 94 is used to apply a force to it than when the second projection 96 is so employed. The projections are accordingly positioned such that the flanged end of a relatively large syringe mounted to the pump will engage first projection 94 while the flanged end of a relatively small syringe will engage second projection 96. A greater force is accordingly required to actuate switch 92 when a large syringe is in place than when a small syringe is employed. This is desirable as a greater force is required to drive the plunger of a large syringe than a small syringe under normal operating conditions. A correspondingly larger force should be necessary to generate an occlusion signal when a large syringe is being emptied than when a small syringe is emptied.

As discussed above, syringe pusher 22 is secured to belt 72. A connecting member 104, as best shown in FIG. 10, extends from housing 78. Connecting member 104 includes three projections 106, 108, 110. Belt 72 is positioned between projections 106, 108, 110 such that the toothed surface thereof engages a toothed surface 112 of lower projection 110 Connecting member 104 extends through an elongate slot 112 (FIG. 1) in housing 12 which adjoins recess 16 in which a syringe may be positioned. A channel 114 is defined by the connecting member. The channel receives the upper edge of a wall of the mid-housing 12B. The opposite end of the syringe pusher 22 includes a projection 116 which rides upon another upper edge of the mid-housing 12B. A relatively narrow, elongate slot 118 is defined within handle 14 for receiving projection 116. Syringe pusher 22 is accordingly supported at both ends by mid-housing 12B.

A resilient, semi-rigid, elongate band 120, as best shown in FIG. 3, is provided for covering slot 112. Band 120 is preferably opaque, and includes a plurality of openings 122 extending through at least a portion thereof. Band 120 is sufficient in length and width to cover the entire slot regardless of the position of syringe pusher 22. A rectangular notch 124 is provided within the band for receiving connecting member 104 of syringe pusher 22. Band 120 is accordingly movable with the syringe pusher about a generally oval path. Mid-housing 12B may include a slotted wall (not shown) for guiding band 120 about the path shown in FIGS. 3 and 4.

Band 120 is preferably employed for several purposes in addition to serving as a liquid barrier It accordingly includes openings 122 which are equidistantly spaced. Lines may be printed upon band 120 in lieu of the openings. A detector 126 as shown in FIGS. 3 and 4 is positioned adjacent to band 120 and detects each opening as the band moves with the syringe pusher. Detector 126 and band openings 122 function in combination to insure that the syringe pusher has not become detached from the belt and that the syringe pusher is, in fact, moving as motor 34 is operating They also allow the injection rate to be determined as the rate at which the openings 122 pass by detector 126 is detected. Portions of band 120 which do not pass by detector 126 need not be provided with openings.

Referring to FIG. 1, a slot 152 is formed within the drive mechanism compartment cover 12D and the mid-housing 12B. A generally curved wall 157 is provided in mid-housing 12B such that a syringe barrel may be placed and clamped against curved wall 157. First and second walls projecting 154, 156 bound slot 152. First wall 154 projects away from the plane of curved wall 157 a distance approximately equal to the thickness of the barrel wall of a syringe. Referring now to FIGS. 3 and 4, a pivotably mounted sensor link 158 is positioned in curved wall 157 just below second wall 156 in opposing relation to the face portion 150 of the slide. Sensor link 158 extends through a slot 159 adjoining the second wall 156, and is engageable by a syringe only if the flange thereof is positioned within slot 152 between walls 154, 156. First wall 154 thus prevents sensor link 158 from being engaged by the barrel of a syringe unless the flange thereof is within slot 152 and the syringe barrel lies flush against curved wall 157. If not so positioned, wall 154 engages the syringe barrel so that it is spaced from the sensor link 158. A detector 160 is positioned adjacent to the sensor link. Detector 160 is closed when the flange of a syringe barrel is properly positioned with slot 152 and barrel wall engages sensor link 158.

Lever 90 and associated switch 92 of the syringe pusher function in conjunction with a second switch 162. This switch 162 is positioned at or slightly above a point corresponding to the position of the plunger of the largest size syringe to be employed within the pump when it reaches the end of the syringe barrel. Switch 162 is closed by connecting member 104 of the syringe pusher 22 as it nears the end of its travel within the recess 16.

The signal provided by switch 162 does not, by itself, cause the pump to stop operating or cause any alarms to be sounded. This is because the signal is generally provided while there is still fluid within the syringe barrel. It is only when switch 92 within the syringe pusher also provides a signal that the motor 34 is shut off and an end of infusion alarm is generated.

Unlike an occlusion, which requires prompt attention, the end of infusion does not ordinarily require immediate action on the part of a medical staff. It is accordingly desirable to distinguish between the alarms to be provided for these respective conditions. Pump 10 accordingly includes the necessary hardware for allowing a more urgent alarm to be generated in the event of occlusions than is generated at the end of infusion. If signals are generated by both switches 92, 162, a non-urgent alarm can be provided. If a signal is received only from the switch 92 within the syringe pusher, a different and more urgent alarm can be generated.

As discussed above, a syringe is positioned within recess 16 such that the flange of the syringe plunger is engaged by lip 82 of swing arm 80 of syringe pusher 22 and the flange of the syringe barrel is positioned within notch 152. Actuation of motor 34 causes rotation of pinion 38, the gears comprising gear reduction assembly 40, and, in turn, drive pulley 74 to which drive belt 72 is mounted. Movement of drive belt 72 causes syringe pusher 22 to move the syringe plunger into the syringe barrel, thereby causing fluid to be displaced outwardly from the barrel. The syringe pusher moves at a steady speed until the syringe barrel has been emptied completely, unless an occlusion occurs beforehand. As it moves, band 120 moves with it, thereby preventing contaminants from entering the pump housing through slot 112. Openings 122 of band 120 are detected by detector 126 in order to insure that syringe pusher 22 is, in fact, moving with belt 72. A typical syringe pusher speed may be about five to six inches per hour, though the pump may be designed to operate at different or variable speeds chosen by the operator, depending upon its intended use.

Assuming normal operation, syringe pusher 22 moves downwardly through recess 16 and closes end of infusion switch 162 when it approaches the end of its travel. Switch 162 is maintained in the closed position while the syringe pusher 22 urges the syringe plunger into engagement with the end of the syringe barrel. Further movement of syringe pusher 22 from this point causes lever 90 to be displaced until it closes "occlusion" switch 92. The closure of "occlusion" switch 92 causes motor 34 to be disconnected from the power supply. Such disconnection may be effected through the use of a microprocessor or mechanical means, the former being preferred.

The use of microprocessors, alarms and displays in connection with medical infusion devices is well known to the art, and need not be discussed in detail with respect to the present invention. U.S. Pat. No. 4,838,857, for example, discloses one such microprocessor-controlled pump having alarms for indicating problems, such as occlusions, and displays for alerting the operator to various pump conditions.

If lever 90 is caused to close "occlusion" switch 92 before end of infusion switch 162 is closed, a signal is generated indicating the occurrence of an occlusion. Such a signal causes a different alarm and/or display to be generated than when "occlusion" switch 92 is closed after the end of infusion switch.

The syringe may be removed once emptied by turning control knob 26 to the "release" position. This action releases both toothed member 130 from slide 134 of the syringe clamp assembly 128 and reduction gear assembly 40 from pinion 38 extending from motor 34. Pusher 22 and swing arm 80 thereof may then be displaced with respect to the syringe plunger, and slide 134 displaced with respect to the pump housing. The syringe is easily removed once these retaining elements have been moved.

FIGS. 12-15B show the pole clamp 30 and the mechanism for moving the pole clamp between a storage position where it is substantially flush with pump housing 12, as shown in FIG. 14B, and a deployed position as shown in FIG. 14A. As discussed above, the pole clamp is operated by turning knob 28 shown in FIGS. 1 and 2.

The pole clamp 30 has a generally L-shaped construction, the longer section thereof being slidably mounted within a recess 164 within base 12A. A generally rectangular opening 166 extends through the longer section of pole clamp 30. A rectangular protrusion 168 extends within opening 166 at a corner thereof.

A wall 170 having a surface 172 including ratchet teeth extends from a surface of pole clamp 30 towards the drive mechanism compartment cover 12D. Wall 170 adjoins the lower edge of the pole clamp 30 and extends below a recessed area 174 therein.

The clamping surface 32 of pole clamp 30 facing the drive mechanism compartment cover 12D includes centrally located recessed area 174 which is bounded by a peripheral wall 176. Opening 166 extends through recessed area 174 while toothed wall 170 extends from peripheral wall 176. A carriage 178 is slidably positioned within recessed area 174. Carriage 178 includes an oval opening 180 which is aligned with a portion of opening 166 extending through pole clamp 30. An arcuate recess 182 is formed within carriage 178 near the inner end thereof. An integral peg 184 extends from carriage, and is located adjacent to the arcuate recess.

A pawl 186 is pivotably mounted to peg 184. Pawl 186 includes a set of ratchet teeth 188 which are engageable with toothed surface 172 of wall 170 extending from pole clamp 30. A peg 190 extends from pawl 186 and into arcuate recess 182. A spring 192 positioned within arcuate recess 182 engages peg 190, thereby urging pawl 186 towards engagement with toothed surface 172 of wall 170. Clamp 30 is thereby releasably locked to carriage 178.

Referring to FIG. 13, the side of pole clamp 30 opposite to wall 170 includes an elongate slot 194 extending along an edge thereof. A peg 196 extends from the inner end of slot 194. As shown in FIGS. 10, 12A and 12B, a slot 198 is provided within base 12A which at least partially overlaps slot 194 in pole clamp 30. A peg 200 extends from one end of slot 198. An extension spring 202 is secured to pegs 196, 200 and resiliently urges pole clamp 30 towards the open position shown in FIG. 14A.

Figure 15A:
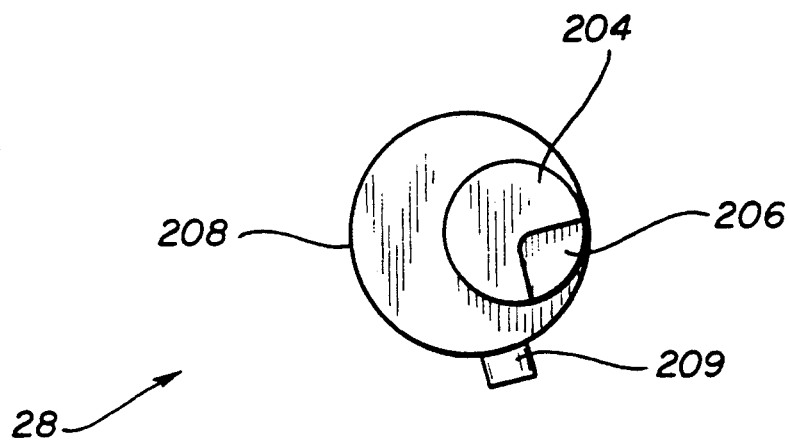
FIG. 15A is a bottom plan view of the eccentric of the pole clamp assembly.
Figure 15B:
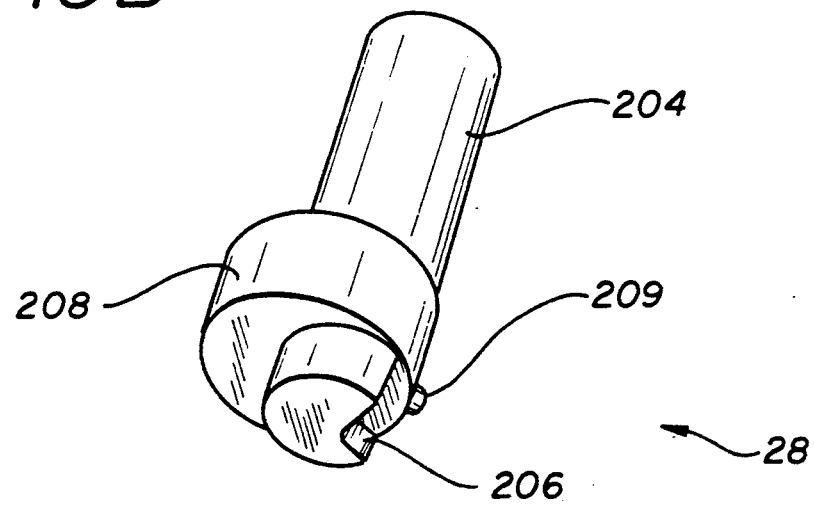
FIG. 15B is a bottom perspective view of the eccentric.

Referring to FIGS. 15A and 15B, knob 28 for controlling the pole clamp 30 is shown without the cap portion thereof. Knob 28 includes a cylindrical shaft 204 having a notch 206 defined in the lower end thereof. The shaft is secured to an eccentric cam 208. The axis of eccentric cam 208 is offset from that of shaft 204 by about an eighth of an inch. Shaft 204 is rotatably fixed to housing 12. Eccentric cam 208 is positioned within oval opening 180 of carriage 178 while the notched end portion extends within elongate opening 166 within pole clamp 30. The purpose of oval opening 180 is simply to provide clearance for eccentric cam 208. Lateral movement of carriage 178 is restricted by the degree to which eccentric is offset from the axis of shaft 204. A peg 209 extends radially from eccentric cam 208.

In operation, pump 10 is placed in adjoining relation to an I.V. pole 210 (shown cut in two for clarity) or the like in the manner shown in FIG. 14A. Pole clamp 30 is manually pushed inwardly until the I.V. pole abuts against both the shorter section of pole clamp 30 and recessed side 212 of the pump. The teeth on upper surface 172 of wall 170 are oriented such that they slide along pawl 186 as pole clamp 30 is moved with respect to carriage 178. The engagement of pawl 186 and surface 172 prevents pole clamp 30 from moving open again under the force of spring 202. Knob 28 is then turned about ninety degrees, causing eccentric cam 208 to move carriage 178 and pole clamp 30 by an additional fraction of an inch (i.e. the offset of the axis of eccentric cam 208 from that of shaft 204) towards pole 210. Clamp 30 is thus tightened against pole 210 which tightly clamped between clamping surface 32 of pole clamp 30 and recessed side 212 of the pump. When knob 28 is rotated by 90° the axes of eccentric cam 208 and shaft 204 are horizontally in line with each other. Since pawl 184 is pivoted at peg 184, at a point above upper surface 172 of wall 172, teeth 188 of pawl 186 will tend to prevent disengagement of pawl 186 from the teeth of upper surface 172.

Pole clamp 30 is constructed such that knob 28 cannot be turned until pole clamp 30 is pushed in towards the I.V. pole from its fully extended position. As shown in FIG. 12A, the protrusion 168 is positioned within notch 206 when pole clamp 30 is fully extended. Knob 28 can only be turned when protrusion 168 is moved out of the notch.

The pump may be removed from the I.V. pole by turning knob 28 in the opposite direction from that used to tighten the clamp. The initial rotation of know 28 causes pole clamp 30 to move outwardly a fraction of an inch due to the movement of eccentric cam 208. Further rotation causes peg 209 extending from eccentric 208 to engage pawl 186 and rotate it about peg 184 extending from carriage 178. The teeth of pawl 186 are thereby disengaged from those of upper surface 172. Upon such disengagement, spring 202 causes pole clamp 30 to move to the fully extended position where the pump can easily be removed from the pole.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A syringe pump comprising a device for detecting a syringe for use in a syringe pump, the syringe comprising a plunger, a barrel defined by a cylindrical wall and a flange projecting from the barrel, the device comprising:

a syringe pump wall against which the syringe can be placed;

a first projection projecting outward from the plane of the syringe pump wall a distance from the syringe pump wall approximately equal to the thickness of the cylindrical wall; and, a detector for detecting the presence of the syringe, the detector mounted to the syringe pump wall a distance from the projection such that the syringe barrel cannot activate the detector when the barrel is placed against the projection.

2. The syringe pump of claim 1 wherein the distance which the projection projects is less than the perpendicular distance from the syringe pump wall to the plunger when the barrel lies flush against the syringe pump wall.

3. The syringe pump of claim 1 wherein the distance from the projection is small relative to the length of the syringe.

4. The syringe pump of claim 1 wherein the syringe pump wall is provided with a slot defining a space inward of the syringe pump wall, the space being adapted to receive the flange of the syringe, such that when the flange is located in the slot, the barrel of the syringe lies flush against the syringe pump wall.

5. The syringe pump of claim 4 wherein the slot is defined by two walls and wherein the projection is an extension of one of the walls.

6. The syringe pump of claim 4 further comprising a second projection projecting away from the syringe pump wall, the second projection being located such that the slot lies between the first projection and the second projection.

7. The syringe pump of claim 6 wherein the detector is located adjacent the second projection.

8. The syringe pump of claim 6 wherein the slot is defined by two first walls and wherein the second projection is an extension of the one of the walls.

9. A syringe pump comprising a device for ensuring the correct placement of a syringe in a syringe pump, the syringe comprising a plunger, a barrel defined by a cylindrical wall and a flange projecting from the barrel, the device comprising:

a syringe pump wall against which the syringe can be placed;

a slot formed in the syringe pump wall for receiving the syringe flange such that when the barrel lies flush against the syringe pump wall, the syringe flange is correctly placed in the slot;

a projection adjacent the slot projecting away from the plane of the syringe pump wall by a distance approximately equal to the thickness of the cylindrical wall;

a detector adjacent the slot, mounted to the pump wall such that the syringe barrel will not activate the detector if the barrel is placed against the projection, but will activate the detector if the flange is placed in the slot and the barrel is flush with the syringe pump wall.

* * * * *